(12) United States Patent
Liang et al.

(10) Patent No.: US 10,035,808 B1
(45) Date of Patent: Jul. 31, 2018

(54) ISATIN PEROXO COMPOUNDS WITH ANTIBACTERIAL ACTIVITIES AND A METHOD OF PREPARING THE SAME

(71) Applicants: Chengyuan Liang, Xi'an (CN); Danni Tian, Xi'an (CN); Minyi Jia, Xi'an (CN)

(72) Inventors: Chengyuan Liang, Xi'an (CN); Danni Tian, Xi'an (CN); Minyi Jia, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 15/957,872

(22) Filed: Apr. 19, 2018

(51) Int. Cl.
*C07D 491/056* (2006.01)

(52) U.S. Cl.
CPC ................ *C07D 491/056* (2013.01)

(58) Field of Classification Search
CPC .................................. C07D 491/056

USPC ........................................... 548/431
See application file for complete search history.

(56) References Cited

U.S. PATENT DOCUMENTS

2010/0217012 A1* 8/2010 Wang ................ C07D 303/23
548/431

\* cited by examiner

*Primary Examiner* — Kristin A Vajda (57) ABSTRACT

An isatin peroxo compound has the following formula (I):

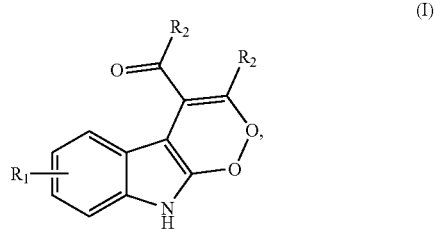

$R_1$ is H, halogen, or $C_{1-3}$ alkyl, and $R_2$, is H, $C_{1-3}$ alkyl, or phenyl.

5 Claims, 2 Drawing Sheets

ISATIN PEROXO COMPOUNDS WITH ANTIBACTERIAL ACTIVITIES AND A METHOD OF PREPARING THE SAME

The present invention claims priority to Chinese Patent Application No. 201810285272.9, filed on Apr. 3, 2018, which is incorporated by reference for all purposes as if fully set forth herein.

FIELD OF THE INVENTION

The present invention relates to the field of medicinal chemistry, and in particular, to isatin peroxo compounds with antibacterial activities and a method of preparing the same.

BACKGROUND OF THE INVENTION

Isatin is an active substance that widely exists in animals, plants and human bodies, and has some antibacterial effects in itself. There are a few drugs that contain isatin core structure:

Sunitinib

Intedanib

Semaxanib

TSU-68

Antibacterial resistance and its association with serious infectious diseases have increased at alarming rates. Thus there remains a need for new antibacterial compounds, particularly those with novel structures and mechanisms of action.

SUMMARY OF THE INVENTION

In one embodiment, the present invention provides an isatin peroxo compound having the following formula (I):

(I)

In formula (I), $R_1$ is H, halogen, or $C_{1-3}$ alkyl, and $R_2$, is H, $C_{1-3}$ alkyl, or phenyl.

In another embodiment, the compound is selected from the group consisting of:

(I)

$R_1$ is H, halogen, or $C_{1-3}$ alkyl, and $R_2$, is H, $C_{1-3}$ alkyl, or phenyl; the non-polar solvent is selected from the group consisting of 1,2-dichloroethane, toluene, and THF; and the catalyst includes an oxidation agent and an acid compound, the oxidation agent is $O_3$, $H_2O_2$, or a mixture of $KMnO_4$/$MnO_2$, and the acid compound is $AlCl_3$, $ZnCl_2$, or a strong acid ion exchange resin.

In another embodiment, a molar ratio of the compound of formula (II) to the compound of formula (III) is 1:1 to 1:1.2.

In another embodiment, the strong acid ion exchange resin is a styrene ionic resin with sulfonic acid group ($—SO_3H$).

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Reference will now be made in detail to embodiments of the present invention.

As used herein, the term $C_{1-3}$ alkyl refers to a monovalent straight or branched chain, saturated aliphatic hydrocarbon radical having 1-3 carbon atoms. For example, $C_{1-3}$ alkyl refers to methyl, ethyl, propyl, and isopropyl. The term halogen refers to fluorine, chlorine, bromine and iodine.

It is an object of the present invention to provide isatin peroxo compounds with antibacterial activities and a method of preparing the same. The method has the advantages of one-pot synthesis, low production cost, high operational safety, mild conditions, high yields, suitable for industrial production. The isatin peroxo compounds can be used in antibacterial research and to treat various bacterial infections.

To achieve the above objects, the technical solution adopted by the present invention is described in details below.

An isatin peroxo compound with antibacterial activities has the following formula (I):

In one embodiment, the present application provides a method of preparing the isatin peroxo compound. The method includes reacting a compound of formula (II) with a compound of formula (III) in a one pot reaction, $R_1$ is H, halogen, or $C_{1-3}$ alkyl, and $R_2$, is H, $C_{1-3}$ alkyl, or phenyl.

An object of the present invention is to provide a method of preparing the isatin peroxo compound of formula (I). The isatin peroxo compound of formula (I) can be prepared by a one-pot synthesis reaction shown below.

$R_1$ is H, halogen, or $C_{1-3}$ alkyl, and $R_2$, is H, $C_{1-3}$ alkyl, or phenyl.

The method includes the following steps:

(1) isatin or an isatin derivative (formula (II)) and a dicarbonyl compound (formula (III)), in a molar ratio of 1:1-1:1.2, were added to a reactor. An appropriate amount of a non-polar solvent and a small amount of DMF (dimethylformamide) were added to the raction, and the mixture was mixed thoroughly. The non-polar solvent can be 1,2-dichloroethane, toluene, or THF (tetrahydrofuran). A catalyst was then added to the mixture, and the mixture was heated at 80-120° C. for 6-12 hours. The catalyst includes an oxidation agent and an acid compound. The oxidation agent can be $O_3$, $H_2O_2$, or a mixture of $KMnO_4/MnO_2$. The acid compound can be $AlCl_3$, $ZnCl_2$, or a strong acid ion exchange resin. The strong acid ion exchange resin can be a styrene ionic resin with sulfonic acid group (—$SO_3H$).

(2) The reaction was monitored with thin layer chromatograph (TLC). When TLC indicated that the reaction was complete, the reaction mixture was removed from heating.

(3) The reaction mixture was concentrated, filtrated, and washed with a non-polar solvent or purified by fresh chromatograph to obtain desired product.

(4) The product was then weighed, and a yield was calculated.

Example 1

The preparation of 1-(3-methyl-9H-[1,2]dioxino[3,4-b]indol-4-yl)ethanone (compound 1).

200 mg (1.36 mmol) isatin, 163.1 mg (1.63 mmol) 2,4-pentanedione, 50 mL 1,2-dichloroethane and 5 mL DMF as solvent, 1 mL $H_2O_2$, and 13.6 mg $AlCl_3$ as catalyst were added to a 100 mL round flask. The mixture was stirred and heated at 100° C. for 12 hours. The reaction was monitored with TLC. When TLC indicated that reaction was complete, heating was removed. The reaction mixture was concentrated, filtered, and washed with 1,2-dichloroethane to obtain 219.9 mg desired product (compound 1), a yield of 70.6%.

Figure 1:
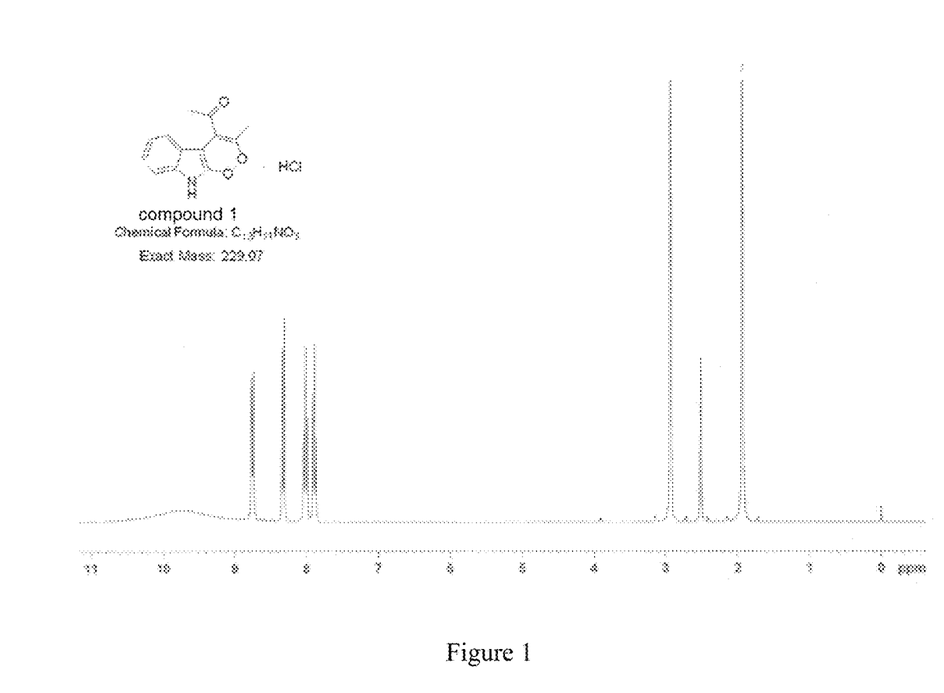
FIG. 1 is $^1$H-NMR spectrum of compound 1.
Figure 2:
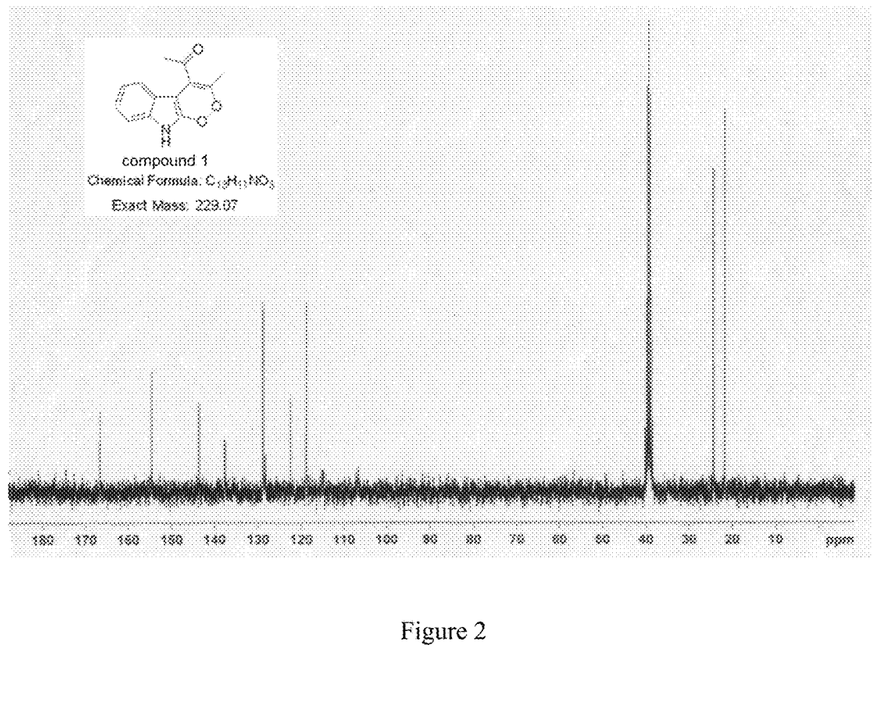
FIG. 2 is $^{13}$C-NMR spectrum of compound 1.

$^1$H-NMR (300 MHz, DMSO-d$^6$) δ (ppm): 9.83 (2H, s), 8.77 (1H, d), 8.34 (1H, d), 8.05 (1H, m), 7.92 (1H, t), 2.93 (3H, s), 1.94 (3H, s) (shown in FIG. 1); $^{13}$C-NMR (7 5 MHz, DMSO-d$^6$) δ (ppm): 166.7, 154.6, 143.7, 137.8, 137.6, 128.9, 128.8, 122.5, 118.9, 118.8, 24.4, 21.7 (shown in FIG. 2); MS (ESI) for (M+H)$^+$: 230.1.

Example 2

The preparation of 1-(6-chloro-3-methyl-9H-[1,2]dioxino[3,4-b]indol-4-yl)ethanone (compound 2).

181 mg (1.0 mmol) 5-chloroisatin, 120.1 mg (1.2 mmol) 2,4-pentanedione, 50 mL toluene and 5 mL DMF as solvent, 1 mL $H_2O_2$, and 20 mg strong acid ion exchange resin D001 as catalyst were added to a 100 mL round flask. The mixture was stirred and heated at 110° C. for 10 hours. The reaction was monitored with TLC. When TLC indicated that reaction was complete, heating was removed. The reaction mixture was concentrated, filtered, and washed with toluene to obtain 195.9 mg desired product (compound 2), a yield of 74.5%.

-continued

5

$^1$H-NMR (300 MHz, DMSO-d$^6$) δ (ppm): 10.25 (1H, s), 7.63 (1H, s), 7.45 (1H, d), 7.16 (1H, d), 2.27 (3H, s), 2.12 (3H, s); $^{13}$C-NMR (75 MHz, DMSO-d$^6$) δ (ppm): 168.5, 162.3, 146.7, 128.5, 125.6, 123.4, 121.7, 118.1, 109.4, 28.9, 11.8; MS (ESI) for (M+Na)$^+$: 286.0.

Example 3

The preparation of 1-(3,6-dimethyl-9H-[1,2]dioxino[3,4-b]indol-4-yl)ethanone (compound 3).

193.2 mg (1.2 mmol) 5-methylisatin, 144.1 mg (1.44 mmol) 2,4-pentanedione, 50 mL THF and 5 mL DMF as solvent, 12.1 mg KMnO$_4$ and 6.7 mg MnO$_2$, and 20 mg strong acid ion exchange resin D001 as catalyst were added to a 100 mL round flask. The mixture was stirred and heated at 80° C. for 12 hours. The reaction was monitored with TLC. When TLC indicated that reaction was complete, heating was removed. The reaction mixture was concentrated, filtered, and washed with THF to obtain 196.0 mg desired product (compound 3), a yield of 67.2%.

$^1$H-NMR (300 MHz, DMSO-d$^6$) δ (ppm): 10.87 (1H, s), 7.81 (1H, s), 7.65 (1H, d), 7.15 (1H, d), 2.34 (3H, s), 2.28 (3H, s), 2.24 (3H, s); $^{13}$C-NMR (75 MHz, DMSO-d$^6$) δ (ppm): 187.3, 185.1, 153.8, 139.5, 128.9, 126.2, 120.8, 111.1, 108.5, 91.1, 22.9, 20.7, 10.8; MS (ESI) for (M+H)$^+$: 244.1.

Example 4

The preparation of phenyl(3-phenyl-9H-[1,2]dioxino[3,4-b]indol-4-yl)methanone (compound 4).

102.9 mg (0.7 mmol) isatin, 188.2 mg (0.84 mmol) 1,3-diphenyl-1,3-propanedione, 50 mL 1,2-dichloroethane and 5 mL DMF as solvent, 1 mL H$_2$O$_2$, and 20 mg strong acid ion exchange resin D001 as catalyst were added to a 100 mL round flask. The mixture was stirred and heated at 90° C. for 11 hours. The reaction was monitored with TLC. When TLC indicated that reaction was complete, heating was removed. The reaction mixture was concentrated, filtered, and purified by fresh chromatograph to obtain 147.8 mg desired product (compound 4), a yield of 59.8%.

$^1$H-NMR (300 MHz, DMSO-d$^6$) δ (ppm): 10.55 (1H, s), 6.91~7.92 (4H, m), 7.23~7.67 (5H, m), 7.62~7.78 (5H, m); $^{13}$C-NMR (75 MHz, DMSO-d$^6$) δ (ppm): 188.5, 158.2, 142.5, 135.9, 134.5, 130.9, 129.2, 127.9, 124.0, 122.7, 119.8, 115.0, 111.3, 100.9, 93.1; MS (ESI) for (M+Na)$^+$: 376.1.

Example 5

The preparation of (6-chloro-3-phenyl-9H-[1,2]dioxino[3,4-b]indol-4-yl)(phenyl)methanone (compound 5).

108.6 mg (0.6 mmol) 5-chloroisatin, 161.3 mg (0.72 mmol) 1,3-diphenyl-1,3-propanedione, 50 mL THF and 5 mL DMF as solvent, 1 mL H$_2$O$_2$, and 13.4 mg AlCl$_3$ as catalyst were added to a 100 mL round flask. The mixture was stirred and heated at 90° C. for 12 hours. The reaction was monitored with TLC. When TLC indicated that reaction was complete, heating was removed. The reaction mixture was concentrated, filtered, and purified by fresh chromatograph to obtain 88.89 mg desired product (compound 5), a yield of 35.7%.

$^1$H-NMR (300 MHz, DMSO-d$^6$) δ (ppm): 10.53 (1H, s), 7.35~7.75 (5H, m), 7.62~7.85 (5H, m), 7.21 (1H, m), 7.02

(1H, m), 6.58 (1H, m); $^{13}$C-NMR (75 MHz, DMSO-d$^6$) δ (ppm): 198.5, 188.5, 152.7, 142.9, 137.9, 134.5, 130.3, 128.8, 128.6, 128.5, 127.9, 127.7, 125.8, 122.2, 119.7, 114.9, 100.5, 92; MS (ESI) for (M+H)$^+$: 388.1.

Example 6

The preparation of (6-methyl-3-phenyl-9H-[1,2]dioxino[3,4-b]indol-4-yl)(phenyl)methanone (compound 6)

128.8 mg (0.8 mmol) 5-methylisatin, 215.1 mg (0.96 mmol) 1,3-diphenyl-1,3-propanedione, 50 mL 1,2-dichloroethane and 5 mL DMF as solvent, 13.7 mg KMnO$_4$ and 8.2 mg MnO$_2$, and 20 mg strong acid ion exchange resin D001 as catalyst were added to a 100 mL round flask. The mixture was stirred and heated at 100° C. for 8 hours. The reaction was monitored with TLC. When TLC indicated that reaction was complete, heating was removed. The reaction mixture was concentrated, filtered, and washed with 1,2-dichloroethane to obtain 86.8 mg desired product (compound 6), a yield of 29.5%.

$^1$H-NMR (300 MHz, DMSO-d$^6$) δ (ppm): 10.85 (1H, s), 7.33~7.77 (5H, m), 7.58~7.89 (5H, m), 7.11 (1H, m), 6.72 (1H, s), 6.52 (1H, d), 2.34 (3H, m); $^{13}$C-NMR (75 MHz, DMSO-d$^6$) δ (ppm): 172.5, 168.5, 153.2, 145.2, 138.9, 135.5, 134.8, 130.3, 129.9, 128.8, 128.5, 127.5, 126.3, 120.9, 111.5, 99.8, 93.0, 22.7; MS (ESI) for (M+Na)$^+$: 390.1.

Example 7

The preparation of 1-(6-fluoro-3-methyl-9H-[1,2]dioxino[3,4-b]indol-4-yl)ethanone (compound 7).

165 mg (1.0 mmol) 5-fluoroisatin, 120.1 mg (1.2 mmol) 2,4-pentanedione, 50 mL THF and 5 mL DMF as solvent, 1 mL H$_2$O$_2$, and 20 mg strong acid ion exchange resin D001 as catalyst were added to a 100 mL round flask. The mixture was stirred and heated at 75° C. for 12 hours. The reaction was monitored with TLC. When TLC indicated that reaction was complete, heating was removed. The reaction mixture was concentrated, filtered, and washed with THF to obtain 156.9 mg desired product (compound 7), a yield of 63.5%.

$^1$H-NMR (300 MHz, DMSO-d$^6$) δ (ppm): 10.54 (1H, s), 6.89 (1H, d), 6.75 (1H, d), 6.54 (1H, s), 2.27 (3H, s), 2.15 (3H, s); $^{13}$C-NMR (75 MHz, DMSO-d$^6$) δ (ppm): 166.5, 165.1, 155.6, 152.8, 138.9, 126.3, 115.2, 108.2, 106.7, 95.1, 22.8, 10.7; MS (ESI) for (M+H)$^+$: 248.1.

Example 8

The preparation of 1-(7-chloro-3-methyl-9H-[1,2]dioxino[3,4-b]indol-4-yl)ethanone (compound 8).

153.8 mg (0.85 mmol) 6-chloroisatin, 102.1 mg (1.02 mmol) 2,4-pentanedione, 50 mL toluene and 5 mL DMF as solvent, 13.6 mg KMnO$_4$ and 7.5 mg MnO$_2$, and 20 mg strong acid ion exchange resin D001 as catalyst were added to a 100 mL round flask. The mixture was stirred and heated at 115° C. for 9 hours. The reaction was monitored with TLC. When TLC indicated that reaction was complete, heating was removed. The reaction mixture was concentrated, filtered, and washed with toluene to obtain 127.2 mg desired product (compound 8), a yield of 56.9%.

$^1$H-NMR (300 MHz, DMSO-d$^6$) δ (ppm): 10.87 (1H, s), 7.21 (1H, d), 6.85 (1H, s), 6.73 (1H, d), 2.28 (3H, s), 2.23 (3H, s); $^{13}$C-NMR (75 MHz, DMSO-d$^6$) δ (ppm): 165.5, 164.1, 153.5, 136.8, 128.4, 126.3, 121.3, 115.9, 106.3, 92.5, 23.9, 11.8; MS (ESI) for (M+Na)$^+$: 286.0.

Example 9

The preparation of 1-(8-fluoro-3-methyl-9H-[1,2]dioxino[3,4-b]indol-4-yl)ethanone (compound 9)

198 mg (1.2 mmol) 7-fluoroisatin, 144.1 mg (1.44 mmol) 2,4-pentanedione, 50 mL THF and 5 mL DMF as solvent, 1 mL H$_2$O$_2$, and 14.5 mg ZnCl$_2$ as catalyst were added to a 100 mL round flask. The mixture was stirred and heated at 85° C. for 12 hours. The reaction was monitored with TLC. When TLC indicated that reaction was complete, heating was removed. The reaction mixture was concentrated, filtered, and washed with THF to obtain 175.5 mg desired product (compound 9), a yield of 59.2%.

$^1$H-NMR (300 MHz, DMSO-d$^6$) δ (ppm): 10.95 (1H, s), 7.59 (1H, d), 6.89 (1H, d), 6.75 (1H, t), 2.38 (3H, s), 2.24 (3H, s); $^{13}$C-NMR (75 MHz, DMSO-d$^6$) δ (ppm): 164.2, 161.1, 153.6, 148.8, 129.9, 126.3, 117.4, 109.9, 106.3, 92.5, 23.9, 11.2; MS (ESI) for (M+H)$^+$: 248.1.

Example 10

Preparation of (6-fluoro-3-phenyl-9H-[1,2]dioxino[3,4-b]indol-4-yl)(phenyl)methanone (compound 10).

115.5 mg (0.7 mmol) 5-fluoroisatin, 188.2 mg (0.84 mmol) 1,3-diphenyl-1,3-propanedione, 50 mL 1,2-dichloroethane and 5 mL DMF as solvent, 1 mL H$_2$O$_2$, and 20 mg strong acid ion exchange resin D001 as catalyst were added to a 100 mL round flask. The mixture was stirred and heated at 100° C. for 9.5 hours. The reaction was monitored with TLC. When TLC indicated that reaction was complete, heating was removed. The reaction mixture was concentrated, filtered, and purified by fresh chromatograph to obtain 152.2 mg desired product (compound 10), a yield of 58.6%.

$^1$H-NMR (300 MHz, DMSO-d$^6$) δ (ppm): 10.68 (1H, $), 7.62~7.91 (5H, m), 7.33~7.78 (5H, m), 6.89 (1H, d), 6.75 (1H, s), 6.69 (1H, s); $^{13}$C-NMR (75 MHz, DMSO-d$^6$) δ (ppm): 170.5, 169.7, 157.6, 138.5, 137.9, 134.5, 131.3, 129.5, 128.6, 127.8, 115.1, 109.8, 100.8, 92.1; MS (ESI) for (M+Na)$^+$: 394.1.

Example 11

The preparation of (7-chloro-3-phenyl-9H-[1,2]dioxino[3,4-b]indol-4-yl)(phenyl)methanone (compound 11).

117.6 mg (0.65 mmol) 6-chloroisatin, 174.8 mg (0.78 mmol) 1,3-diphenyl-1,3-propanedione, 50 mL THF and 5 mL DMF as solvent, 1 mL H$_2$O$_2$, and 14.7 mg AlCl$_3$ as catalyst were added to a 100 mL round flask. The mixture was stirred and heated at 70° C. for 12 hours.

The reaction was monitored with TLC. When TLC indicated that reaction was complete, heating was removed. The reaction mixture was concentrated, filtered, and purified by fresh chromatograph to obtain 64.1 mg desired product (compound 11), a yield of 21.5%.

$^1$H-NMR (300 MHz, DMSO-d$^6$) δ (ppm): 10.76 (1H, s), 7.65~7.89 (5H, m), 7.23~7.82 (5H, m), 7.25 (1H, d), 6.95 (1H, s), 6.81 (1H, d); $^{13}$C-NMR (75 MHz, DMSO-d$^6$) δ (ppm): 174.8, 169.5, 152.3, 137.9, 136.8, 134.5, 131.3, 129.2, 128.8, 128.5, 128.2, 127.8, 125.2, 121.3, 119.5, 111.9, 100.7, 92.5; MS (ESI) for (M+H)$^+$: 388.1.

Example 12

The preparation of (8-fluoro-3-phenyl-9H-[1,2]dioxino[3,4-b]indol-4-yl)(phenyl)methanon (compound 12).

132 mg (0.8 mmol) 7-fluoroisatin, 215.1 mg (0.96 mmol) 1,3-diphenyl-1,3-propanedione, 50 mL toluene and 5 mL DMF as solvent, 1 mL H$_2$O$_2$, and 20 mg strong acid ion exchange resin D001 as catalyst were added to a 100 mL round flask. The mixture was stirred and heated at 110° C. for 8.5 hours. The reaction was monitored with TLC. When TLC indicated that reaction was complete, heating was removed. The reaction mixture was concentrated, filtered, and purified by fresh chromatograph to obtain 190.6 mg desired product (compound 12), a yield of 64.2%.

$^1$H-NMR (300 MHz, DMSO-d$^6$) δ (ppm): 10.89 (1H, s), 7.68~7.85 (5H, m), 7.22~7.67 (5H, m), 7.14 (1H, d), 6.85 (1H, d), 6.75 (1H, t); $^{13}$C-NMR (75 MHz, DMSO-d$^6$) δ (ppm): 169.2, 167.5, 153.2, 148.9, 136.5, 134.5, 132.7, 130.3, 129.2, 128.8, 127.9, 122.1, 118.4, 108.5, 100.9, 93.3; MS (ESI) for (M+Na)$^+$: 394.1.

Example 13

Antibacterial activity test of the compounds of the invention

The compounds of the present invention have been tested for antibacterial activity, and a bacteriostatic circle method was used to determine the antibacterial activity.

Test strains and medium: Enteropathogenic *Escherichia coli* (EPEC), Enterotoxigenic *Escherichia coli* (ETEC), Enteroinvasive *Escherichia coli* (EIEC), Enterohemorrhagic *Escherichia coli* (EHEC); beef peptone medium.

Preparation of Test Strains:

Preparation of test strains: (1) test strains were placed in culture medium in test tubes in an incubator (bacteria: 37° C., 24 hours; fungi: 28° C., 48 hours), and stored at 0-4° C.; (2) the test strains were inoculated with a small loop in test tubes containing 9 mL sterile water, mixing well to make suspensions, and adjusting the concentration to 106-107 cfu·mL$^{-1}$. The suspensions were used for bacteriostatic circle test.

Antibacterial activity determination: solvent dimethyl sulfoxide (DMSO) was used as a negative control, the sizes of antibacterial ring diameters indicated the strength of the antibacterial activities.

The test results are shown in Table 1.

TABLE 1

Results of Bacteriostatic Circle Test

| Compounds/Control | Circle Size/mm Strands | | | |
|---|---|---|---|---|
| | EPEC | ETEC | EIEC | EHEC |
| DMSO | 0 | 0 | 0 | 0 |
| Compound 1 | 20 | 19 | 21 | 23 |
| Compound 2 | 15 | 15.5 | 17 | 16.5 |
| Compound 3 | 17.5 | 18 | 17 | 17 |
| Compound 4 | 12 | 11 | 11.5 | 12.5 |
| Compound 5 | 13 | 13.5 | 14 | 14.5 |
| Compound 6 | 15 | 15.5 | 16 | 16 |
| Compound 7 | 17 | 17.5 | 16.5 | 17 |
| Compound 8 | 13 | 14 | 13.5 | 13 |
| Compound 9 | 15 | 15.5 | 14 | 14.5 |
| Compound 10 | 10 | 11 | 11.5 | 10.5 |
| Compound 11 | 12 | 12.5 | 11.5 | 11.5 |
| Compound 12 | 14 | 14.5 | 14.5 | 15 |

Compound 1 showed good antibacterial activities in all the four tested bacteria, followed by compounds 2 and 3, which also showed good antibacterial activities. The above experimental results show that the compounds of the present invention have good antibacterial activities and can be further used as antibacterial drug candidates for preclinical studies.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. An isatin peroxo compound having the following formula (I):

wherein R$_1$ is H, halogen, or C$_{1-3}$ alkyl, and R$_2$, is H, C$_{1-3}$ alkyl, or phenyl.

2. The isatin peroxo compound of claim 1, wherein the compound is selected from the group consisting of:

-continued

3. A method of preparing the isatin peroxo compound of claim 1 comprising:

reacting a compound of formula (II) with a compound of formula (III) in a one pot reaction, wherein $R_1$ is H, halogen, or $C_{1-3}$ alkyl, and $R_2$, is H, $C_{1-3}$ alkyl, or phenyl;

wherein the non-polar solvent is selected from the group consisting of 1,2-dichloroethane, toluene, and THF; and wherein the catalyst includes an oxidation agent and an acid compound, the oxidation agent is $O_3$, $H_2O_2$, or a mixture of $KMnO_4/MnO_2$, and the acid compound is $AlCl_3$, $ZnCl_2$, or a strong acid ion exchange resin.

4. The method of the claim 3, wherein a molar ratio of the compound of formula (II) to the compound of formula (III) is 1:1 to 1:1.2.

5. The method of claim 4, wherein the strong acid ion exchange resin is a styrene ionic resin with sulfonic acid group (—$SO_3H$).

* * * * *